(12) United States Patent
Watanabe et al.

(10) Patent No.: US 11,531,014 B2
(45) Date of Patent: Dec. 20, 2022

(54) GAS SENSOR AND GAS SENSOR OPERATION CONTROL METHOD

(71) Applicant: NGK INSULATORS, LTD., Nagoya (JP)

(72) Inventors: Yusuke Watanabe, Nagoya (JP); Takayuki Sekiya, Nisshin (JP); Daichi Ichikawa, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 153 days.

(21) Appl. No.: 16/998,003

(22) Filed: Aug. 20, 2020

(65) Prior Publication Data
US 2021/0063369 A1   Mar. 4, 2021

(30) Foreign Application Priority Data

Aug. 28, 2019 (JP) .............................. JP2019-155704
Jun. 17, 2020 (JP) .............................. JP2020-104695

(51) Int. Cl.
*G01N 27/419* (2006.01)
*G01N 33/00* (2006.01)
*G01N 27/407* (2006.01)

(52) U.S. Cl.
CPC ...... *G01N 33/0037* (2013.01); *G01N 27/4074* (2013.01); *G01N 27/419* (2013.01)

(58) Field of Classification Search
CPC ........... G01N 33/0037; G01N 27/4074; G01N 27/419; Y02A 50/20
See application file for complete search history.

(56) References Cited

U.S. PATENT DOCUMENTS 5,763,763 A    6/1998 Kato et al.
6,645,367 B1 * 11/2003 Zhang ................ G01N 27/4175
                                            204/426

(Continued)

FOREIGN PATENT DOCUMENTS

EP       1075657 B1 *  5/2008 ......... G01N 27/4175
GB       2345142 A  *  6/2000 ......... F02D 41/1441

(Continued)

OTHER PUBLICATIONS

Norikazu et al, translation of JP 2010151804 A, 2010 (Year: 2010).*

*Primary Examiner* — Joshua L Allen
*Assistant Examiner* — Shizhi Qian
(74) *Attorney, Agent, or Firm* — Mattingly & Malur, PC

(57) ABSTRACT

A controller of the gas sensor can perform diagnostic processing of diagnosing a situation of control to the gas sensor in a case that the gas sensor in an operation state is determined to satisfy a predetermined diagnostic condition and adjustment processing of adjusting a condition for controlling the gas sensor in accordance with a result of diagnosis. In the diagnostic processing, a main pump voltage and a diagnostic threshold as a value of a voltage not causing decomposition of NOx in the main pump cell are compared. In the adjustment processing, temperature adjustment processing to cause, in a case that the main pump voltage is diagnosed to be equal to the threshold or more, the main pump voltage to be less than the threshold, at least in a way that the heater part increases the element driving temperature in the operation state by a predetermined increase amount is performed.

10 Claims, 11 Drawing Sheets

(56) References Cited

U.S. PATENT DOCUMENTS

2009/0242427 A1* 10/2009 Muraguchi .......... G01N 27/419
                                                                    205/781
2017/0336342 A1* 11/2017 Abe .................. G01N 33/0036

FOREIGN PATENT DOCUMENTS

| JP | 3050781 B2 | 6/2000 | |
| JP | 2010151804 A * | 7/2010 | ........... G01N 27/407 |
| JP | 2014-190940 A | 10/2014 | |
| JP | 2014-209128 A | 11/2014 | |

\* cited by examiner

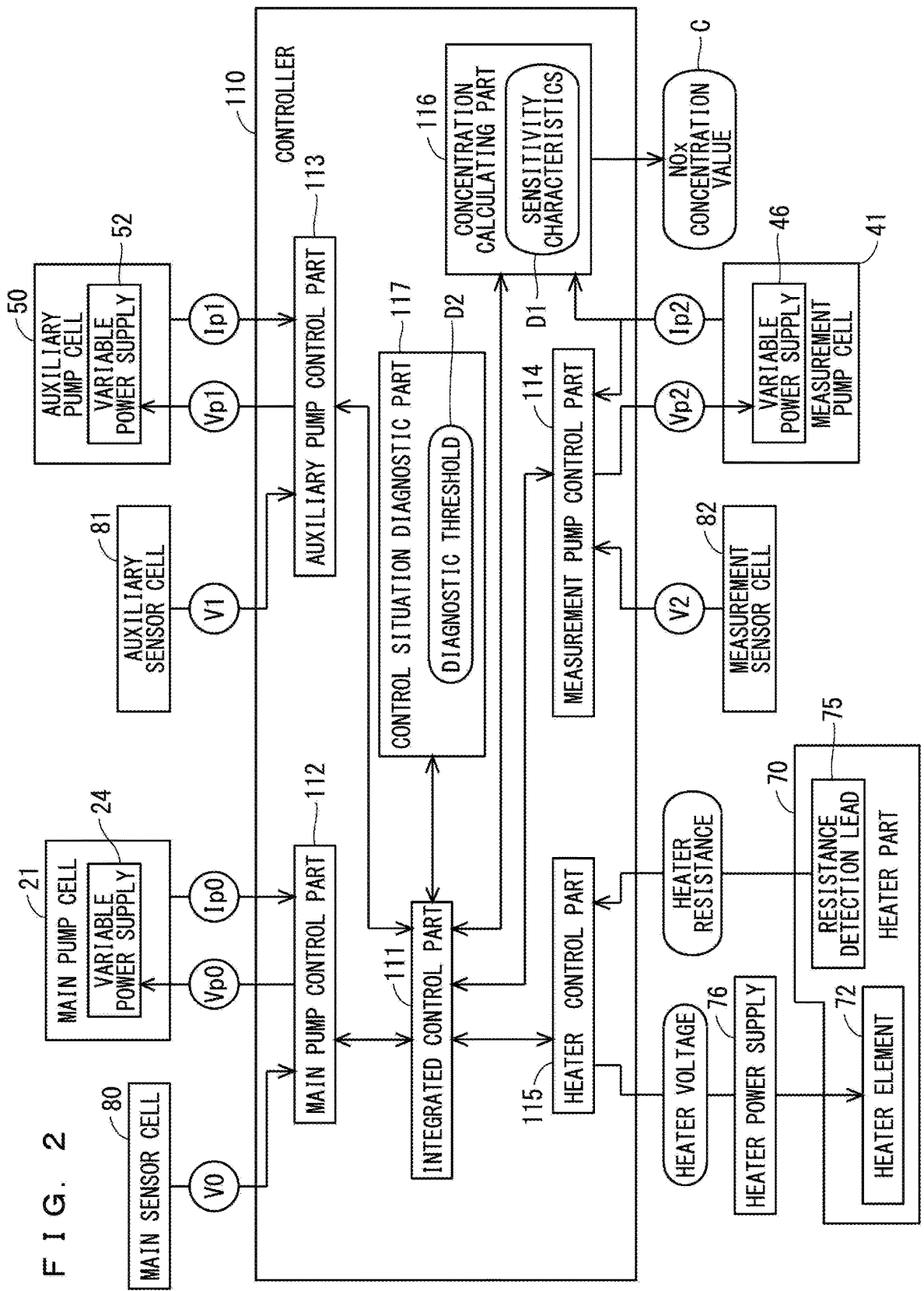
F I G. 2

F I G. 6
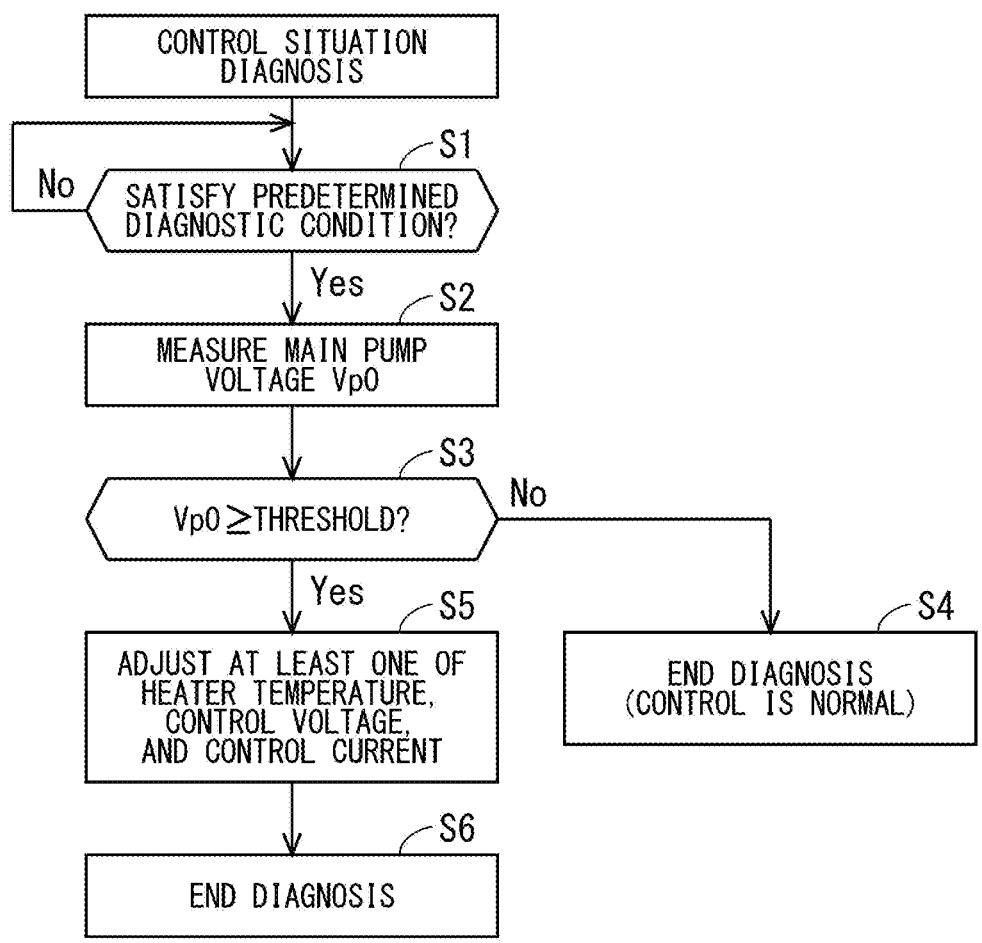

F I G. 7
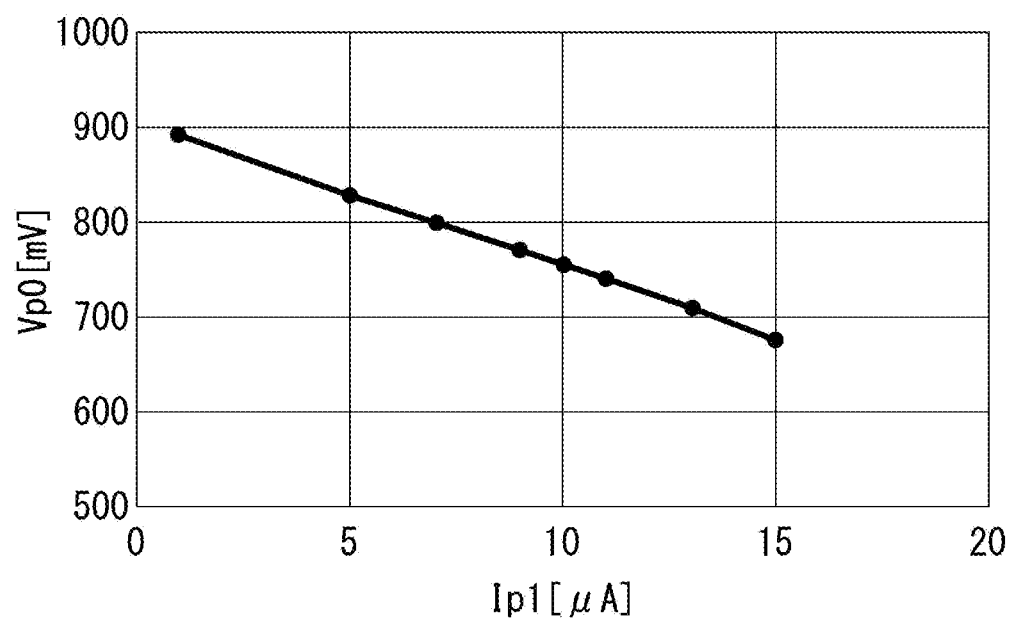

F I G. 8
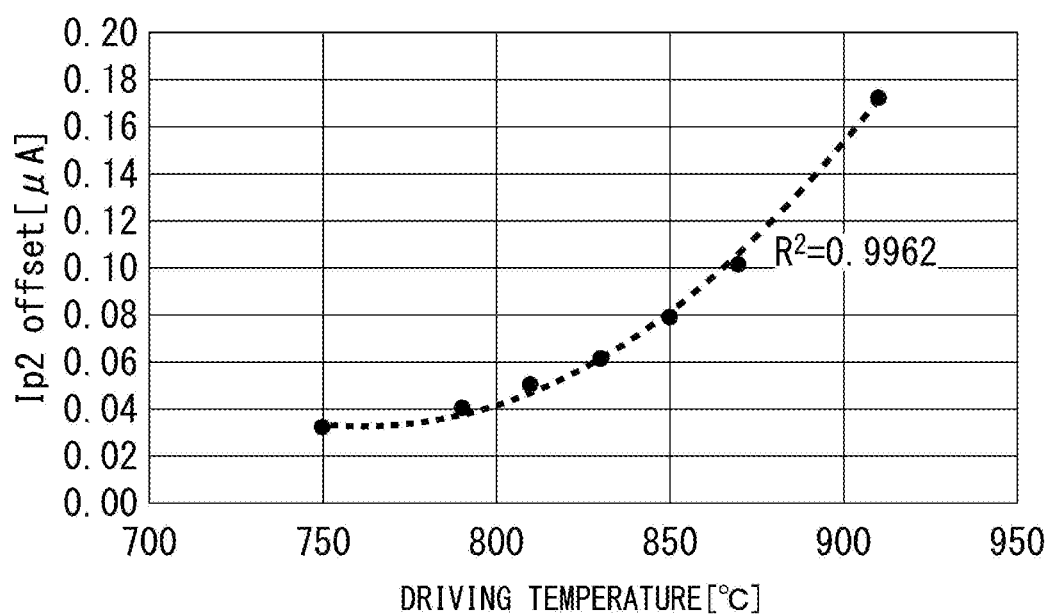

F I G. 9
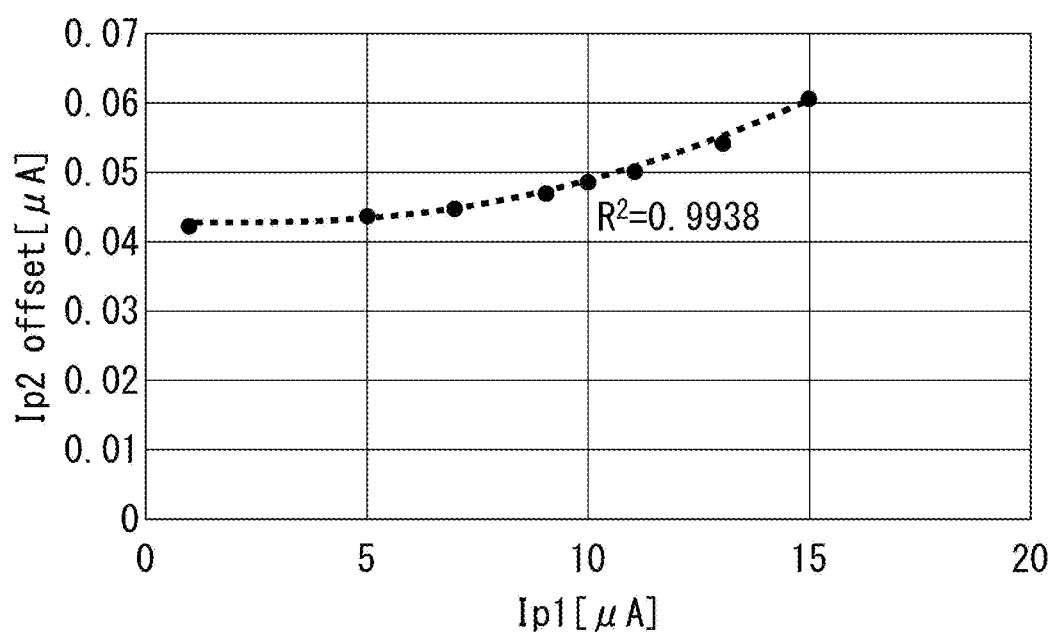

GAS SENSOR AND GAS SENSOR OPERATION CONTROL METHOD

CROSS-REFERENCE TO RELATED APPLICATION

The present application claims priority from Japanese applications JP 2019-155704, filed on Aug. 28, 2019 and JP 2020-104695, filed on Jun. 17, 2020, the contents of which is hereby incorporated by reference into this application.

BACKGROUND OF THE INVENTION

Field of the Invention

The present invention relates to a gas sensor for determining concentration of nitrogen oxides (NOx), and, in particular, to operation control to secure measurement accuracy in a high NOx concentration range.

Description of the Background Art

A limiting-current type gas sensor (NOx sensor) including a sensor element containing an oxygen-ion conductive solid electrolyte as a main component has already been known (see, for example, Japanese Patent No. 3050781). In determining a NOx concentration using such a gas sensor, a measurement gas is first introduced into a space (an internal space) inside the sensor element under predetermined diffusion resistance, and oxygen in the measurement gas is pumped out by a two-stage electrochemical pump cell, for example, referred to as a main pump cell and an auxiliary pump cell (a first electrochemical pump cell and a second electrochemical pump cell in Japanese Patent No. 3050781) to sufficiently reduce an oxygen concentration of the measurement gas in advance. NOx in the measurement gas is then reduced or decomposed by a measurement electrode (third inner pump electrode in Japanese Patent No. 3050781) functioning as a reduction catalyst, and oxygen thus generated is pumped out by an electrochemical pump cell (a third electrochemical pump cell in Japanese Patent No. 3050781) different from the above-mentioned electrochemical pump cell, including the measurement electrode, and, for example, referred to as a measurement pump cell. The NOx concentration is determined using a constant functional relationship between a current (NOx current) flowing through the measurement pump cell and the NOx concentration.

In the gas sensor (NOx sensor), use of Pt to which Au has been added (an Au—Pt alloy) as a metal component of an inner pump electrode located in the internal space and forming the main pump cell to suppress decomposition of NOx caused when the main pump cell pumps out oxygen from the internal space and to enhance NOx detection accuracy has already been known (see, for example, Japanese Patent Application Laid-Open No. 2014-190940 and Japanese Patent Application Laid-Open No. 2014-209128).

In a gas sensor as described above, the NOx concentration is determined based on the amount of oxygen generated through reduction of NOx in the measurement gas having reached the measurement electrode caused by catalytic action of the measurement electrode. In this case, oxygen in the measurement gas is pumped out by the electrochemical pump cell before the measurement gas reaches the measurement electrode, and the pumping out of oxygen is performed to sufficiently reduce oxygen partial pressure (the oxygen concentration) of the measurement gas to the extent not causing decomposition of NOx. If NOx is decomposed before reaching the measurement electrode, the amount of NOx reaching the measurement electrode is reduced to make it difficult to determine the concentration thereof with accuracy.

In a case where the measurement gas introduced into the internal space has a high oxygen concentration, however, NOx might be decomposed when oxygen is pumped out. In this respect, it has been found from intensive studies made by the inventors of the present invention that, in a gas sensor in which impedance of the main pump cell increases due to deterioration of the main pump electrode and a heater, a pump voltage applied to the main pump cell tends to increase and, as a result, decomposition of NOx is likely to be caused.

SUMMARY

The present invention relates to a gas sensor for determining concentration of nitrogen oxides (NOx), and is, in particular, directed to operation control to secure measurement accuracy in a high NOx concentration range.

According to the present invention, a limiting-current type gas sensor measuring concentration of NOx in a measurement gas includes: a sensor element having a base part made of an oxygen-ion conductive solid electrolyte and including: a gas inlet through which the measurement gas is introduced from an external space; a first internal space communicating with the gas inlet under predetermined diffusion resistance; a main pump cell as an electrochemical pump cell including an inner pump electrode located to face the first internal space, an out-of-space pump electrode located to face a space other than the first internal space, and the solid electrolyte located between the inner pump electrode and the out-of-space pump electrode; a measurement electrode located inside the sensor element, at least one diffusion control part being located between the measurement electrode and the first internal space; a measurement pump cell as an electrochemical pump cell including the measurement electrode, the out-of-space pump electrode, and the solid electrolyte located between the measurement electrode and the out-of-space pump electrode; a reference electrode located inside the sensor element and capable of being in contact with a reference gas; and a heater part buried in the sensor element and heating the sensor element; and a controller controlling operation of the gas sensor and including: a determination element configured to perform condition determination processing of determining whether the gas sensor satisfies a predetermined diagnostic condition when the gas sensor is in an operation state capable of measuring a NOx concentration; a diagnostic element configured to perform diagnostic processing of diagnosing a situation of control to the gas sensor in a case that the gas sensor is determined to satisfy the diagnostic condition; and an adjustment element configured to perform adjustment processing of adjusting a condition under which the gas sensor is controlled in accordance with a result of diagnosis in the diagnostic processing, wherein the gas sensor is put into the operation state capable of measuring the NOx concentration at least when: the heater part heats the sensor element to a predetermined element driving temperature; a main pump voltage is applied to the main pump cell so that an oxygen concentration in the first internal space is constant; and a measurement pump voltage is applied to the measurement pump cell so that oxygen generated through decomposition of NOx in the measurement electrode is pumped out, in the diagnostic processing, the diagnostic element compares the main pump voltage and a diagnostic threshold set in advance as a value of a voltage not causing decomposition of NOx in the main pump cell, the adjustment element includes a temperature adjustment element performing temperature adjustment processing as the adjustment processing, and the temperature adjustment processing is processing to cause, in a case that the main pump voltage is diagnosed to be equal to the diagnostic threshold or more in the diagnostic processing, the main pump voltage to be less than the diagnostic threshold, at least in a way that the heater part increases the element driving temperature in the operation state by a predetermined increase amount.

Accordingly, operation control to the sensor element in the gas sensor performed in an inappropriate situation in which decomposition of NOx is caused in the main pump cell is suitably suppressed. Even in a gas sensor in which, due to deterioration over time, the main pump voltage increases in a case where the measurement gas has a high oxygen concentration, and thus decomposition of NOx might be caused in the main pump cell, NOx can be measured with accuracy while suppressing the decomposition.

The controller preferably further includes a concentration calculating element configured to obtain a value of the concentration of NOx in the measurement gas based on a magnitude of a current flowing through the measurement pump cell, and the concentration calculating element corrects the value of the concentration of NOx obtained by the concentration calculating element based on at least one of the element driving temperature after the increase in the temperature adjustment processing and the auxiliary pump current after the increase in the auxiliary pump current adjustment processing.

In this case, reduction in NOx measurement accuracy due to suppressing decomposition of NOx in the main pump cell is suitably suppressed.

It is thus an object of the present invention to provide a gas sensor capable of measuring NOx with accuracy even in a case where a measurement gas has a high oxygen concentration.

These and other objects, features, aspects and advantages of the present invention will become more apparent from the following detailed description of the present invention when taken in conjunction with the accompanying drawings.

BRIEF DESCRIPTION OF THE DRAWINGS

FIG. 2 shows a functional configuration of a controller 110;

FIG. 6 shows a flow of control situation diagnostic processing performed in the gas sensor 100;

FIG. 7 shows an example of a relationship between an auxiliary pump current Ip1 and the main pump voltage Vp0;

FIG. 8 shows an example of a relationship between a heater temperature and an actual value of an offset current;

FIG. 9 shows an example of a relationship between a control current and the actual value of the offset current;

DESCRIPTION OF THE PREFERRED EMBODIMENTS

First Embodiment

<General Configuration of Gas Sensor>

A general configuration of a gas sensor 100 including a sensor element 101 according to a first embodiment of the present invention will be described first. In the present embodiment, the gas sensor 100 is a limiting-current type NOx sensor to sense NOx and measure concentration thereof using the sensor element 101. The gas sensor 100 further includes a controller 110 to control operation of each part and identify the NOx concentration based on a NOx current flowing through the sensor element 101.

Figure 1:
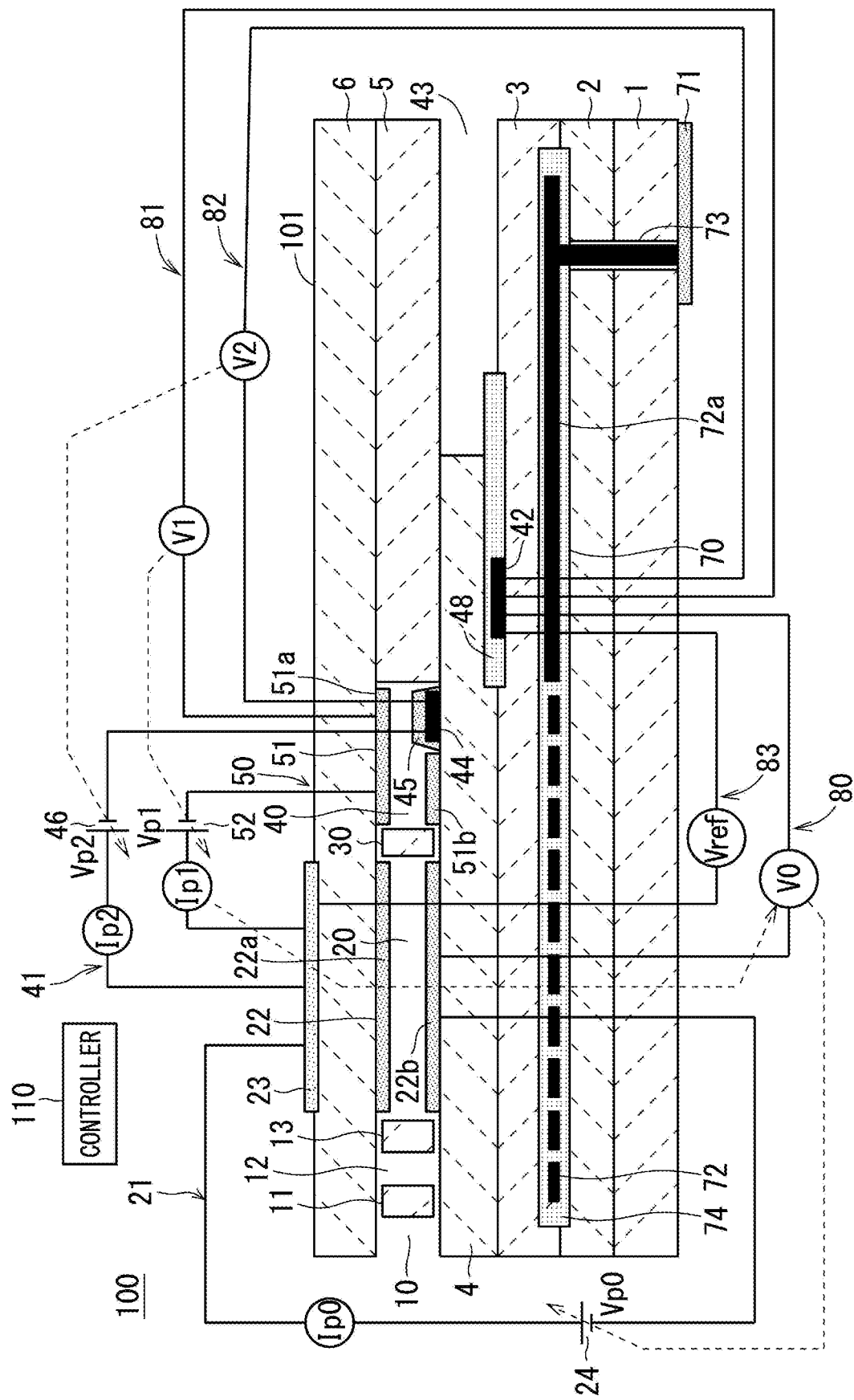
FIG. 1 schematically shows one example of a configuration of a gas sensor 100 including a vertical sectional view taken along a longitudinal direction of a sensor element 101.

FIG. 1 schematically shows one example of a configuration of the gas sensor 100 including a vertical sectional view taken along a longitudinal direction of the sensor element 101.

The sensor element 101 is a planar (elongated planar) element having a structure in which six solid electrolyte layers, namely, a first substrate layer 1, a second substrate layer 2, a third substrate layer 3, a first solid electrolyte layer 4, a spacer layer 5, and a second solid electrolyte layer 6 each made of zirconia ($ZrO_2$) (e.g., yttrium stabilized zirconia (YSZ)) as an oxygen-ion conductive solid electrolyte are laminated in the stated order from a bottom side of FIG. 1. The solid electrolyte forming these six layers is dense and airtight. A surface on an upper side and a surface on a lower side of each of these six layers in FIG. 1 are hereinafter also simply referred to as an upper surface and a lower surface, respectively. A part of the sensor element 101 made of the solid electrolyte as a whole is generically referred to as a base part.

The sensor element 101 is manufactured, for example, by performing predetermined processing, printing of circuit patterns, and the like on ceramic green sheets corresponding to the respective layers, then laminating them, and further firing them for integration.

Between a lower surface of the second solid electrolyte layer 6 and an upper surface of the first solid electrolyte layer 4 in one leading end portion of the sensor element 101, a gas inlet 10, a first diffusion control part 11, a buffer space 12, a second diffusion control part 13, a first internal space 20, a third diffusion control part 30, and a second internal space 40 are formed adjacent to each other to communicate in the stated order.

The gas inlet 10, the buffer space 12, the first internal space 20, and the second internal space 40 are spaces inside the sensor element 101 looking as if they were provided by hollowing out the spacer layer 5, and having an upper portion, a lower portion, and a side portion respectively defined by the lower surface of the second solid electrolyte layer 6, the upper surface of the first solid electrolyte layer 4, and a side surface of the spacer layer 5.

The first diffusion control part 11, the second diffusion control part 13, and the third diffusion control part 30 are each provided as two horizontally long slits (whose openings have longitudinal directions perpendicular to the page of FIG. 1). A part extending from the gas inlet 10 to the second internal space 40 is also referred to as a gas distribution part.

At a location farther from the leading end than the gas distribution part is, a reference gas introduction space 43 having a side portion defined by a side surface of the first solid electrolyte layer 4 is provided between an upper surface of the third substrate layer 3 and a lower surface of the spacer layer 5. For example, air is introduced into the reference gas introduction space 43 as a reference gas when the NOx concentration is measured.

An air introduction layer 48 is a layer made of porous alumina, and the reference gas is introduced into the air introduction layer 48 through the reference gas introduction space 43. The air introduction layer 48 is formed to cover a reference electrode 42.

The reference electrode 42 is an electrode formed to be sandwiched between the upper surface of the third substrate layer 3 and the first solid electrolyte layer 4, and the air introduction layer 48 leading to the reference gas introduction space 43 is provided around the reference electrode 42 as described above. As will be described below, an oxygen concentration (oxygen partial pressure) in the first internal space 20 and the second internal space 40 can be measured using the reference electrode 42.

In the gas distribution part, the gas inlet 10 is a part opening to an external space, and a measurement gas is taken from the external space into the sensor element 101 through the gas inlet 10.

The first diffusion control part 11 is a part providing predetermined diffusion resistance to the measurement gas taken through the gas inlet 10.

The buffer space 12 is a space provided to guide the measurement gas introduced from the first diffusion control part 11 to the second diffusion control part 13.

The second diffusion control part 13 is a part providing predetermined diffusion resistance to the measurement gas introduced from the buffer space 12 into the first internal space 20.

In introducing the measurement gas from outside the sensor element 101 into the first internal space 20, the measurement gas having abruptly been taken into the sensor element 101 through the gas inlet 10 due to pressure fluctuations (pulsation of exhaust pressure in a case where the measurement gas is an exhaust gas of a vehicle) of the measurement gas in the external space is not directly introduced into the first internal space 20 but is introduced into the first internal space 20 after concentration fluctuations of the measurement gas are canceled through the first diffusion control part 11, the buffer space 12, and the second diffusion control part 13. This makes the concentration fluctuations of the measurement gas introduced into the first internal space 20 almost negligible.

The first internal space 20 is provided as a space to adjust oxygen partial pressure of the measurement gas introduced through the second diffusion control part 13. The oxygen partial pressure is adjusted by operating a main pump cell 21.

The main pump cell 21 is an electrochemical pump cell including an inner pump electrode 22, an outer (out-of-space) pump electrode 23, and the second solid electrolyte layer 6 sandwiched between these electrodes. The inner pump electrode 22 has a ceiling electrode portion 22a provided on substantially the entire lower surface of a portion of the second solid electrolyte layer 6 facing the first internal space 20, and the outer pump electrode 23 is provided in a region, on an upper surface of the second solid electrolyte layer 6 (one main surface of the sensor element 101), corresponding to the ceiling electrode portion 22a to be exposed to the external space.

The inner pump electrode 22 is formed on upper and lower solid electrolyte layers (the second solid electrolyte layer 6 and the first solid electrolyte layer 4) defining the first internal space 20. Specifically, the ceiling electrode portion 22a is formed on the lower surface of the second solid electrolyte layer 6, which provides a ceiling surface to the first internal space 20, and a bottom electrode portion 22b is formed on the upper surface of the first solid electrolyte layer 4, which provides a bottom surface to the first internal space 20. The ceiling electrode portion 22a and the bottom electrode portion 22b are connected by a conducting portion (not illustrated) provided on a side wall surface (an inner surface) of the spacer layer 5 forming opposite side wall portions of the first internal space 20.

The ceiling electrode portion 22a and the bottom electrode portion 22b are provided to be rectangular in plan view. Only the ceiling electrode portion 22a or only the bottom electrode portion 22b may be provided.

The inner pump electrode 22 and the outer pump electrode 23 are each formed as a porous cermet electrode. In particular, the inner pump electrode 22 to be in contact with the measurement gas is formed using a material having a weakened reducing ability with respect to a NOx component in the measurement gas. The inner pump electrode 22 is formed, for example, as a cermet electrode of an Au—Pt alloy containing Au of approximately 0.6 wt % to 1.4 wt % and $ZrO_2$ to have a porosity of 5% to 40% and a thickness of 5 μm to 20 μm. The Au—Pt alloy and $ZrO_2$ are only required to have a weight ratio Pt:$ZrO_2$ of approximately 7.0:3.0 to 5.0:5.0.

On the other hand, the outer pump electrode 23 is formed, for example, as a cermet electrode of Pt or an alloy thereof and $ZrO_2$ to be rectangular in plan view.

The main pump cell 21 can pump out oxygen in the first internal space 20 to the external space or pump in oxygen in the external space to the first internal space 20 by applying, from a variable power supply 24, a desired pump voltage Vp0 between the inner pump electrode 22 and the outer pump electrode 23 to allow a main pump current Ip0 to flow between the inner pump electrode 22 and the outer pump electrode 23 in a positive or negative direction. The pump voltage Vp0 applied between the inner pump electrode 22 and the outer pump electrode 23 by the main pump cell 21 is also referred to as a main pump voltage Vp0.

To detect the oxygen concentration (oxygen partial pressure) in an atmosphere in the first internal space 20, the inner pump electrode 22, the second solid electrolyte layer 6, the spacer layer 5, the first solid electrolyte layer 4, the third substrate layer 3, and the reference electrode 42 constitute a main sensor cell 80 as an electrochemical sensor cell.

The oxygen concentration (oxygen partial pressure) in the first internal space 20 can be known by measuring electromotive force V0 in the main sensor cell 80.

Furthermore, the controller 110 performs feedback control of the main pump voltage Vp0 so that the electromotive force V0 is constant, thereby to control the main pump current Ip0. The oxygen concentration in the first internal space 20 is thereby maintained to have a predetermined constant value.

The third diffusion control part 30 is a part providing predetermined diffusion resistance to the measurement gas having an oxygen concentration (oxygen partial pressure) controlled by operation of the main pump cell 21 in the first internal space 20, and guiding the measurement gas to the second internal space 40.

The second internal space 40 is provided as a space to perform processing concerning measurement of the nitrogen oxide (NOx) concentration of the measurement gas introduced through the third diffusion control part 30. The NOx concentration is measured, mainly in the second internal space 40 in which the oxygen concentration has been adjusted by an auxiliary pump cell 50, further by operation of a measurement pump cell 41.

After the oxygen concentration (oxygen partial pressure) is adjusted in advance in the first internal space 20, the auxiliary pump cell 50 further adjusts the oxygen partial pressure of the measurement gas introduced through the third diffusion control part 30 in the second internal space 40. The oxygen concentration in the second internal space 40 can thereby be maintained constant with high accuracy, and thus the NOx concentration can be measured with high accuracy in the gas sensor 100.

The auxiliary pump cell 50 is an auxiliary electrochemical pump cell including an auxiliary pump electrode 51, the outer pump electrode 23 (not limited to the outer pump electrode 23 and only required to be any appropriate electrode outside the sensor element 101), and the second solid electrolyte layer 6. The auxiliary pump electrode 51 has a ceiling electrode portion 51a provided substantially on the entire lower surface of a portion of the second solid electrolyte layer 6 facing the second internal space 40.

The auxiliary pump electrode 51 is provided in the second internal space 40 in a similar form to the inner pump electrode 22 provided in the first internal space 20 described previously. That is to say, the ceiling electrode portion 51a is formed on the second solid electrolyte layer 6, which provides a ceiling surface to the second internal space 40, and a bottom electrode portion 51b is formed on the first solid electrolyte layer 4, which provides a bottom surface to the second internal space 40. The ceiling electrode portion 51a and the bottom electrode portion 51b are rectangular in plan view, and are connected by a conducting portion (not illustrated) provided on the side wall surface (inner surface) of the spacer layer 5 forming opposite side wall portions of the second internal space 40.

As with the inner pump electrode 22, the auxiliary pump electrode 51 is formed using a material having a weakened reducing ability with respect to the NOx component in the measurement gas.

The auxiliary pump cell 50 can pump out oxygen in an atmosphere in the second internal space 40 to the external space or pump in oxygen in the external space to the second internal space 40 by applying a desired voltage Vp1 between the auxiliary pump electrode 51 and the outer pump electrode 23 under control performed by the controller 110.

To control the oxygen partial pressure in the atmosphere in the second internal space 40, the auxiliary pump electrode 51, the reference electrode 42, the second solid electrolyte layer 6, the spacer layer 5, the first solid electrolyte layer 4, and the third substrate layer 3 constitute an auxiliary sensor cell 81 as an electrochemical sensor cell.

The auxiliary pump cell 50 performs pumping using a variable power supply 52 whose voltage is controlled based on electromotive force V1 detected in the auxiliary sensor cell 81 in accordance with the oxygen partial pressure in the second internal space 40. The oxygen partial pressure in the atmosphere in the second internal space 40 is thereby controlled to a low partial pressure having substantially no effect on measurement of NOx.

At the same time, a resulting auxiliary pump current Ip1 is used to control the electromotive force in the main sensor cell 80. Specifically, the auxiliary pump current Ip1 is input, as a control signal, into the main sensor cell 80, and, through control of the electromotive force V0 therein, the oxygen partial pressure of the measurement gas introduced through the third diffusion control part 30 into the second internal space 40 is controlled to have a gradient that is always constant. In use as the NOx sensor, the oxygen concentration in the second internal space 40 is maintained to have a constant value of approximately 0.001 ppm by the action of the main pump cell 21 and the auxiliary pump cell 50.

The measurement pump cell 41 measures the NOx concentration of the measurement gas in the second internal space 40. The measurement pump cell 41 is an electrochemical pump cell including a measurement electrode 44, the outer pump electrode 23, the second solid electrolyte layer 6, the spacer layer 5, and the first solid electrolyte layer 4. The measurement electrode 44 is provided on an upper surface of a portion of the first solid electrolyte layer 4 facing the second internal space 40 to be separated from the third diffusion control part 30.

The measurement electrode 44 is a porous cermet electrode. The measurement electrode 44 is formed, for example, as a cermet electrode of Pt or an alloy thereof and $ZrO_2$. The measurement electrode 44 also functions as a NOx reduction catalyst to reduce NOx existing in the atmosphere in the second internal space 40. Furthermore, the measurement electrode 44 is covered with a fourth diffusion control part 45.

The fourth diffusion control part 45 is a film formed of a porous body containing alumina ($Al_2O_3$) as a main component. The fourth diffusion control part 45 plays a role in limiting the amount of NOx flowing into the measurement electrode 44, and also functions as a protective film of the measurement electrode 44.

The measurement pump cell 41 can pump out oxygen generated through decomposition of NOx in an atmosphere around the measurement electrode 44, and detect the amount of generated oxygen as a pump current Ip2 under control performed by the controller 110.

To detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute a measurement sensor cell 82 as an electrochemical sensor cell. A variable power supply 46 is controlled based on electromotive force V2 detected in the measurement sensor cell 82 in accordance with the oxygen partial pressure around the measurement electrode 44.

The measurement gas introduced into the second internal space 40 is to reach the measurement electrode 44 through the fourth diffusion control part 45 under a situation in which the oxygen partial pressure is controlled. NOx in the measurement gas around the measurement electrode 44 is reduced ($2NO \rightarrow N_2+O_2$) to generate oxygen. Oxygen as generated is to be pumped by the measurement pump cell 41, and, at this time, a voltage Vp2 of the variable power supply 46 is controlled so that the electromotive force V2 detected in the measurement sensor cell 82 is constant. The amount of oxygen generated around the measurement electrode 44 is proportional to the NOx concentration of the measurement gas, and thus the NOx concentration of the measurement gas is to be calculated using the pump current Ip2 in the measurement pump cell 41. The pump current Ip2 is hereinafter also referred to as a NOx current Ip2.

If the measurement electrode 44, the first solid electrolyte layer 4, the third substrate layer 3, and the reference electrode 42 are combined to constitute an oxygen partial pressure detection means as an electrochemical sensor cell, electromotive force can be detected in accordance with a difference between the amount of oxygen generated through reduction of a NOx component in the atmosphere around the measurement electrode 44 and the amount of oxygen contained in reference air, and the concentration of the NOx component in the measurement gas can thereby be determined.

The second solid electrolyte layer 6, the spacer layer 5, the first solid electrolyte layer 4, the third substrate layer 3, the outer pump electrode 23, and the reference electrode 42 constitute an electrochemical sensor cell 83, and oxygen partial pressure of the measurement gas outside the sensor can be detected using electromotive force Vref obtained by the sensor cell 83.

The sensor element 101 further includes a heater part 70 playing a role in temperature adjustment of heating the sensor element 101 and maintaining the temperature thereof to enhance oxygen ion conductivity of the solid electrolyte forming the base part.

The heater part 70 mainly includes a heater electrode 71, a heater element 72, a heater lead 72a, a through hole 73, a heater insulating layer 74, and a heater resistance detection lead 75 (FIG. 2), which is not illustrated in FIG. 1. A portion of the heater part 70 other than the heater electrode 71 is buried in the base part of the sensor element 101.

The heater electrode 71 is an electrode formed to be in contact with a lower surface of the first substrate layer 1 (the other main surface of the sensor element 101).

The heater element 72 is a resistive heating element provided between the second substrate layer 2 and the third substrate layer 3. The heater element 72 generates heat by being powered from a heater power supply 76 (FIG. 2), which is not illustrated in FIG. 1, outside the sensor element 101 through the heater electrode 71, the through hole 73, and the heater lead 72a, which constitute a current-carrying path. The heater element 72 is made of Pt, or contains Pt as a main component. The heater element 72 is buried, in a predetermined range of the sensor element 101 in which the gas distribution part is provided, to oppose the gas distribution part along the thickness of the element. The heater element 72 is provided to have a thickness of approximately 10 μm to 20 μm.

In the sensor element 101, each part of the sensor element 101 can be heated to a predetermined temperature and the temperature is maintained by allowing a current to flow through the heater electrode 71 to the heater element 72 to thereby cause the heater element 72 to generate heat. Specifically, the sensor element 101 is heated so that the solid electrolyte and the electrodes in the vicinity of the gas distribution part are at a temperature of approximately 700° C. to 900° C. The oxygen ion conductivity of the solid electrolyte forming the base part in the sensor element 101 is enhanced by the heating. A heating temperature of the heater element 72 when the gas sensor 100 is in use (when the sensor element 101 is driven) is referred to as a sensor element driving temperature.

A degree of heat generation of the heater element 72 is grasped by the magnitude of a resistance value (heater resistance) of the heater element 72. The heater resistance detection lead 75 is provided to measure the heater resistance.

<Controller>

Functions of the controller 110 will be described in more detail next. FIG. 2 shows a functional configuration of the controller 110 of the gas sensor 100.

The controller 110 is achieved by a general-purpose or dedicated computer, and includes, as functional components achieved by a CPU, memory, and the like thereof, an integrated control part 111, a main pump control part 112, an auxiliary pump control part 113, a measurement pump control part 114, a heater control part 115, a concentration calculating part 116, and a control situation diagnostic part 117. In a case where NOx contained in exhaust from an engine of a vehicle is a target of sensing and measurement of the gas sensor 100, and the sensor element 101 is installed onto an exhaust path, some or all the functions of the controller 110 may be achieved by an electronic control unit (ECU) mounted on the vehicle.

The integrated control part 111 integrally controls various types of processing performed in the controller 110. That is to say, the integrated control part 111 integrally controls operation for control performed by each of the above-mentioned control parts of the controller 110 toward each of the pump cells, the heater, and the like for sensing of NOx, calculating the concentration, and the like, and controls calculating processing performed by the concentration calculating part 116 and diagnostic processing performed by the control situation diagnostic part 117.

The main pump control part 112 controls operation of the main pump cell 21. Specifically, the main pump control part 112 acquires a value of the electromotive force V0 generated in the main sensor cell 80 in accordance with the oxygen partial pressure in the first internal space 20, performs feedback control of the main pump voltage Vp0 to be applied from the variable power supply 24 to the main pump cell 21 so that the value of the electromotive force V0 is in accordance with desired oxygen partial pressure, and acquires a value of the main pump current Ip0 flowing through the main pump cell 21 at that time.

The auxiliary pump control part 113 controls operation of the auxiliary pump cell 50. Specifically, the auxiliary pump control part 113 acquires a value of the electromotive force V1 generated in the auxiliary sensor cell 81 in accordance with the oxygen partial pressure in the second internal space 40, performs feedback control of the main pump voltage Vp1 to be applied from the variable power supply 52 to the auxiliary pump cell 50 so that the value of the electromotive force V1 is in accordance with desired oxygen partial pressure, and acquires a value of the auxiliary pump current Ip1 flowing through the auxiliary pump cell 50 at that time.

The measurement pump control part 114 controls operation of the measurement pump cell 41. Specifically, the measurement pump control part 114 acquires a value of the electromotive force V2 generated in the measurement sensor cell 82 in accordance with the oxygen partial pressure near the measurement electrode 44, performs feedback control of the measurement pump voltage Vp2 to be applied from the variable power supply 46 to the measurement pump cell 41 so that the value of the electromotive force V2 is in accordance with desired oxygen partial pressure, and acquires a value of the pump current (NOx current) Ip2 flowing through the measurement pump cell 41 at that timing.

The heater control part 115 controls operation of the heater part 70. Specifically, the heater control part 115 controls a heater voltage to be applied to the heater power supply 76 so that a value of the heater resistance (resistance of the heater element 72) obtained as the resistance value between the heater resistance detection lead 75 and the heater lead 72a is in accordance with a desired heating temperature. The heater element 72 generates heat so that the amount of heat generation is in accordance with the heater resistance controlled in this manner. The heater control part 115 controls the value of the heater resistance in accordance with the desired sensor element driving temperature, so that the sensor element driving temperature is achieved.

The concentration calculating part 116 acquires the value of the pump current (NOx current) Ip2 flowing through the measurement pump cell 41, calculates the NOx concentration based on sensitivity characteristics data D1 in which sensitivity characteristics set in advance for the sensor element 101 are described, and outputs the calculated NOx concentration.

In the gas sensor 100, oxygen contained in the measurement gas is pumped out by operating the main pump cell 21 and further the auxiliary pump cell 50 through the main pump control part 112 and the auxiliary pump control part 113, and the measurement gas having oxygen partial pressure sufficiently reduced to a degree (e.g., 0.0001 ppm to 1 ppm) having substantially no effect on measurement of NOx reaches the measurement electrode 44. NOx in the measurement gas having reached the measurement electrode 44 is reduced to generate oxygen. Oxygen as generated is pumped out by the measurement pump cell 41 under control performed by the measurement pump control part 114. A constant functional relationship between the NOx current Ip2 flowing at the pumping out and the concentration of NOx in the measurement gas is referred to as sensitivity characteristics.

The sensitivity characteristics are identified in advance using a plurality of types of model gases having known NOx concentrations prior to actual use of the gas sensor 100, and data thereof is stored as the sensitivity characteristics data D1 in the controller 110 (more particularly, in memory functioning as the concentration calculating part 116).

In actual use of the gas sensor 100, a signal representing the value of the NOx current Ip2 flowing in accordance with the NOx concentration of the measurement gas is momentarily provided to the concentration calculating part 116, and the concentration calculating part 116 successively calculates NOx concentrations based on the value and the identified sensitivity characteristics, and outputs values thereof (NOx concentration values) to the outside the controller 110. The NOx concentration of the measurement gas can thereby be known in almost real time using the gas sensor 100.

Figure 3:
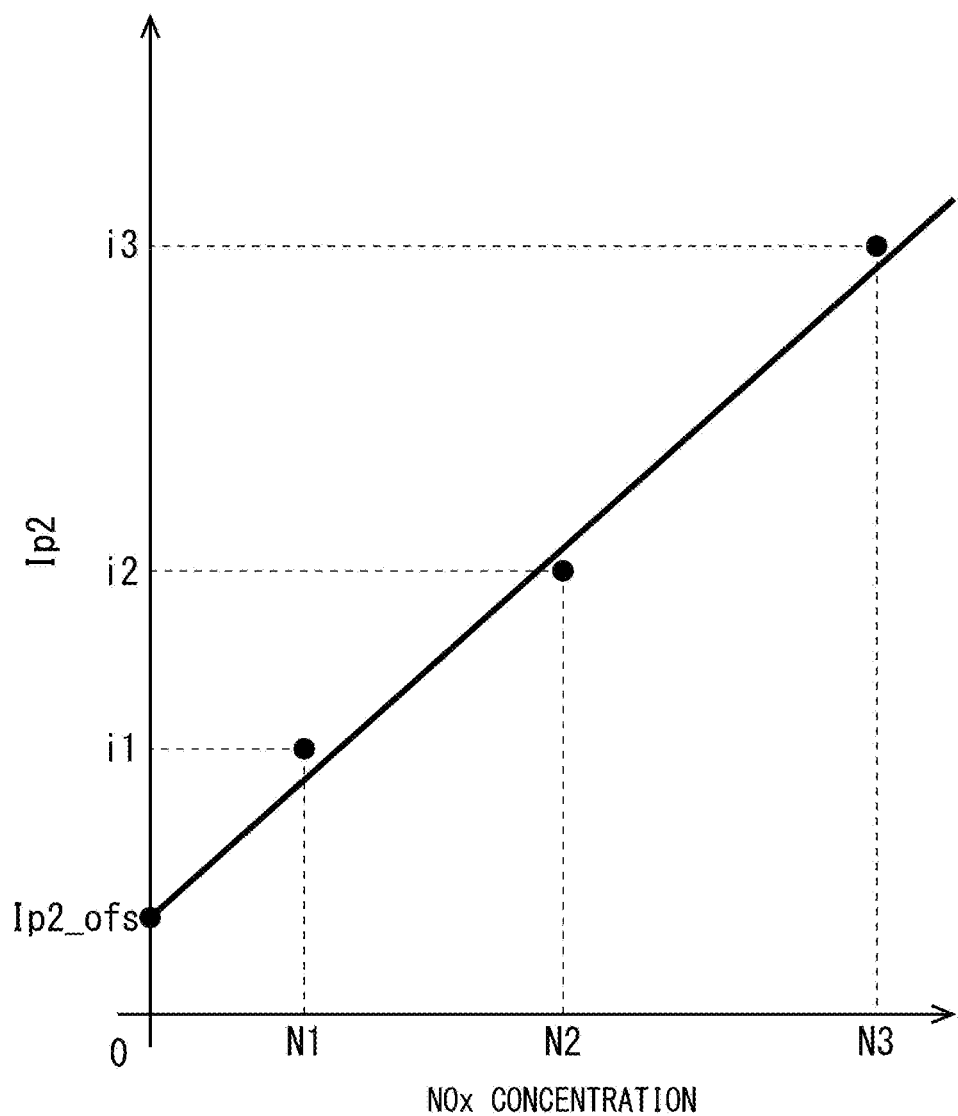
FIG. 3 shows an example of a functional relationship between a NOx concentration and a NOx current Ip2 showing sensitivity characteristics.

FIG. 3 shows an example of the functional relationship between the NOx concentration and the NOx current Ip2 showing the sensitivity characteristics. More specifically, in FIG. 3, i1, i2, and i3 are respective values of the NOx current (current flowing through the measurement pump cell 41) Ip2 when measurement targeted at model gases containing NOx having known concentrations N1, N2, and N3, containing oxygen (or further water) having known concentrations, and containing nitrogen as the balance is performed using the gas sensor 100.

Furthermore, in FIG. 3, Ip2_ofs is a value of the current Ip2 flowing through the measurement pump cell 41 (the current is referred to as the NOx current Ip2 for the sake of convenience) when measurement targeted at a model gas containing similar components except for not containing NOx (i.e., having a NOx concentration of 0) is similarly performed. This NOx current Ip2 when the NOx concentration is 0 is, in particular, referred to as an offset current.

The offset current corresponds to a current flowing when a small amount of oxygen remaining in the measurement gas having reached the measurement electrode 44, in other words, oxygen having reached the measurement electrode 44 without being decomposed by the main pump cell 21 and the auxiliary pump cell 50, is pumped out by the measurement pump cell 41. A smaller offset current is preferable, but the offset current is approximately 0.2 μA at most.

In FIG. 3, a straight line (linear function) having the value Ip2_ofs as a vertical intercept which indicates the relationship between the NOx concentration and the NOx current Ip2, that is, the sensitivity characteristics, is shown. An equation of the straight line can be identified through regression analysis.

A way to identify the sensitivity characteristics is not limited to that in the above-mentioned example. For example, regression analysis may be performed without fixing the measurement value obtained using the model gas not containing NOx as the intercept. In this case, a value of the intercept in the identified straight-line equation is an offset current value.

The sensitivity characteristics may be identified as a curve instead of being identified as the straight line.

The control situation diagnostic part 117 diagnoses a situation in which the sensor element 101 is controlled with the controller 110. The controller 110 can perform control situation diagnostic processing in which the integrated control part 111 changes an operation condition of each part of the sensor element 101 based on a result of diagnosis in the control situation diagnostic part 117. Diagnostic threshold data D2 in which a diagnostic threshold to be used at the control situation diagnostic processing is described is stored in advance in the controller 110 (more particularly, in memory functioning as the control situation diagnostic part 117). The control situation diagnostic processing will be described in detail below.

<Relationship Between Main Pump Voltage and Decomposition of NOx>

Figure 4:
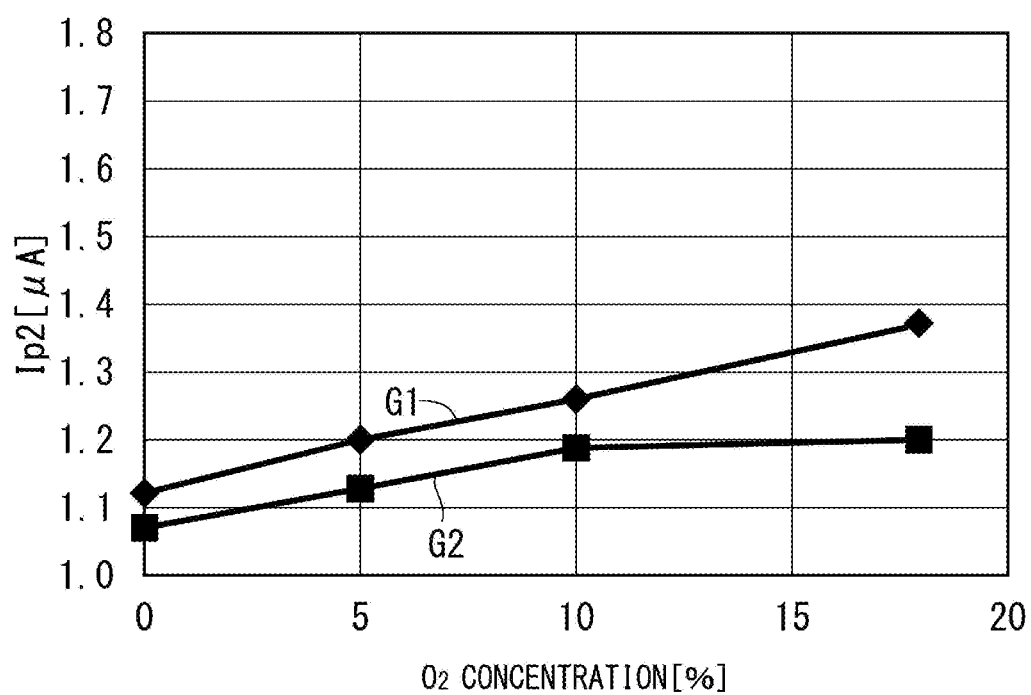
FIG. 4 is a plot of NOx currents Ip2 obtained through model gas measurement using two gas sensors 100 in different states against oxygen concentrations of model gases.

FIG. 4 is a plot of NOx currents Ip2 against the oxygen concentrations of the model gases, in which the NOx currents Ip2 are obtained through measurement (hereinafter, referred to as model gas measurement) targeted at four model gases having different oxygen concentrations of 0%, 5%, 10%, and 18% while having a constant NO concentration of 500 ppm (the balance being $N_2$ in each of the model gases) using two gas sensors 100 in different states. The sensor element driving temperature was 800° C.

Specifically, a graph G1 is a plot of results of measurement using a new gas sensor 100, and a graph G2 is a plot of results of measurement using a gas sensor 100 obtained by placing a new sensor element 101 in air, and conducting a continuous operation test for 3000 hours at the above-mentioned element driving temperature. The continuous operation test is positioned as a (an accelerated) durability test to evaluate a degree of deterioration over time. The term "new" does not necessarily mean "completely unused". Use for about several hours is accepted.

As shown in FIG. 4, in the graph G1, there is a linear change of a monotonous increase between the NOx current Ip2 and the oxygen concentration. A determination coefficient (a value of the square of a correlation coefficient) $R^2$ as obtained was 0.999, which indicates a substantially straight line. In the other graph G2, a value of the NOx current Ip2 is generally smaller than that in the graph G1, and levels off when the oxygen concentration is between 10% and 18% while having a tendency to monotonously increase when the oxygen concentration is 10% or less. The determination coefficient $R^2$ can be considered as an indicator of stability of a pumping ability in the main pump cell 21 with respect to a change in oxygen concentration.

The results suggest that, in the gas sensor 100 having been used for a long time or continuously, a measurement value of the NOx current Ip2 is smaller than that in the new gas sensor 100, and furthermore, in a case where the measurement gas has a high oxygen concentration, NOx in the measurement gas can be decomposed at a stage before reaching the measurement electrode 44 (e.g., in the first internal space 20).

Figure 5:
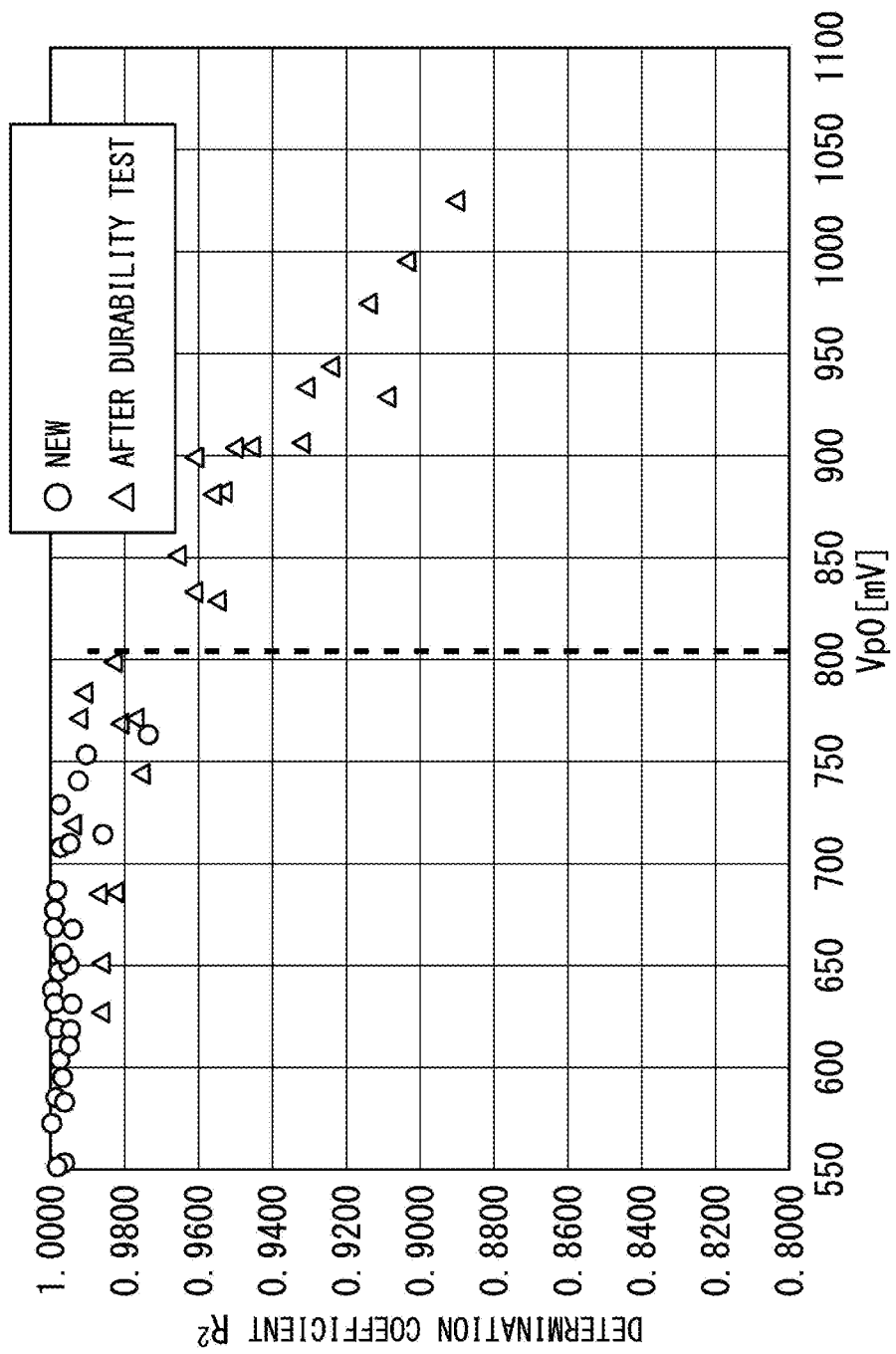
FIG. 5 shows a correlation between a determination coefficient $R^2$ and a main pump voltage Vp0 applied in a case where a measurement gas has a high oxygen concentration in a main pump cell 21.

FIG. 5 shows a correlation between the determination coefficient $R^2$ and the main pump voltage Vp0 applied in a case where the measurement gas has a high oxygen concentration in the main pump cell 21. Specifically, model gas measurement targeted at many new gas sensors 100 and many gas sensors 100 after undergoing the continuous operation test under the same condition as the above-mentioned condition is conducted, a value of the determination coefficient $R^2$ is obtained from the correlation between the NOx current Ip2 and the oxygen concentration as in FIG. 4 obtained based on results of the model gas measurement, and the value of the determination coefficient $R^2$ as obtained is plotted against the main pump voltage Vp0 in the model gas measurement in which the oxygen concentration is set to 18%, thereafter to obtain FIG. 5.

The main pump voltage Vp0 is originally a value to be dynamically changed, for example, in actual use of the gas sensor 100 so that the value of the electromotive force V0 in the main sensor cell 80 changing in accordance with the oxygen concentration of the measurement gas is controlled to be constant, and increases with increasing oxygen concentration.

In a case where the measurement gases having a constant oxygen concentration as in the above-mentioned model gas measurement are targets of measurement, however, the main pump voltage Vp0 has a substantially constant value in accordance with the oxygen concentration in each of the gas sensors 100.

In a case of the above-mentioned model gas measurement targeted at the model gases having four different oxygen concentrations, the main pump voltage Vp0 has a maximum value when the oxygen concentration is set to 18%. On the other hand, NOx is more likely to be decomposed in the main pump cell 21 when the main pump voltage Vp0 has a higher value.

It can thus be said that FIG. 5 shows a correlation between stability of the pumping ability in the main pump cell 21 with respect to the change in oxygen concentration of the measurement gas and an upper limit of the main pump voltage Vp0 at pumping in the main pump cell 21 and further likelihood of decomposition of NOx in the main pump cell 21.

It can be seen from FIG. 5 that, in a case of the new gas sensors 100, the main pump voltage Vp0 is in a range of approximately 760 mV or less, and, particularly in a case where the main pump voltage Vp0 is 700 mV or less, the determination coefficient $R^2$ is approximately 0.99 or more.

This indicates that, in the case of the new gas sensors 100, the main pump cell 21 has excellent stability with respect to the change in oxygen concentration of the measurement gas, oxygen can suitably be pumped without excessively increasing the main pump voltage Vp0 even in a high oxygen concentration range, and decomposition of NOx is not caused in the main pump cell 21.

In contrast, it can be seen that, in a case of the gas sensors 100 after the continuous operation test, the determination coefficient $R^2$ falls within a range of approximately 0.98 or more as long as the main pump voltage Vp0 is in a range of approximately 800 mV or less, and falls within a range of 0.95 or more when the main pump voltage Vp0 is in a range of 900 mV or less, but, as for the gas sensors 100 in which the main pump voltage Vp0 can exceed 900 mV, the determination coefficient $R^2$ decreases significantly with increasing main pump voltage Vp0. It has been confirmed that the decrease in determination coefficient $R^2$ is caused due to leveling off of the NOx current Ip2 in the high oxygen concentration range caused by decomposition of NOx in the main pump cell 21 as in the graph G2 shown in FIG. 4.

The results suggest that, in the gas sensor 100 deteriorated by continuous use, the main pump voltage Vp0 tends to increase at least in the high oxygen concentration range, and further, as for the gas sensor 100 in which the main pump voltage Vp0 can exceed 800 mV, NOx in the measurement gas can be decomposed at the stage before reaching the measurement electrode 44 (e.g., in the first internal space 20) in the case where the measurement gas has a high oxygen concentration.

In the gas sensor 100 according to the present embodiment, in light of these findings, the control situation diagnostic processing that the situation in which the sensor element 101 is controlled is diagnosed based on the magnitude of the main pump voltage Vp0, and that a condition for controlling the sensor element 101 is adjusted as appropriate based on the result of diagnosis can be performed. Details thereof will be described next.

The graph G1 in FIG. 4 shows that, in a case where pumping in the main pump cell 21 is appropriate, the value of the NOx current Ip2 tends to depend on the oxygen concentration of the measurement gas. Such dependency shown in spite of a constant NOx concentration of the model gases suggests that, in determining the NOx concentration based on the sensitivity characteristics, correction using the oxygen concentration is effective to determine the NOx concentration with more accuracy. This can be achieved, for example, by correcting the NOx current Ip2 based on information (e.g., the main pump current Ip0 and the electromotive force Vref) indicating the oxygen concentration of the measurement gas.

<Control Situation Diagnostic Processing>

FIG. 6 shows a flow of the control situation diagnostic processing performed in the gas sensor 100. The control situation diagnostic processing is generally processing to diagnose whether operation control to the sensor element 100 by the controller 110 is performed in an inappropriate situation in which the value of the main pump voltage Vp0 excessively increases when the measurement gas has a high oxygen concentration, and decomposition of NOx is caused in the main pump cell 21, and, in a case where the control is performed in such a situation, to adjust the control condition so that the value of the main pump voltage Vp0 is suppressed.

As described above, the main pump voltage Vp0 is the value to be dynamically changed in accordance with the oxygen concentration of the measurement gas in actual use of the gas sensor 100, and, in a case where the control condition on which the change is based, such as the value of the electromotive force V0 in the main sensor cell 80, is changed, a possible range of the main pump voltage Vp0 can be changed accordingly. The control situation diagnostic processing in the present embodiment utilizes it to suppress the increase in main pump voltage Vp0 to be applied to the main pump cell 21 and prevent decomposition of NOx in the measurement gas in the main pump cell 21.

In the control situation diagnostic processing, the control situation diagnostic part 117 first determines whether a diagnostic condition, which is a precondition for performing the control situation diagnostic processing, is satisfied (step S1). For example, the diagnostic condition is that the temperature of the sensor element 101 has reached the element driving temperature, and the measurement gas at least temporarily becomes an air atmosphere and only air (having an oxygen concentration of approximately 21%) is introduced into the sensor element 101. In a case where the sensor element 101 is installed onto the exhaust path of the vehicle, the diagnostic condition is satisfied, for example, at fuel cut. The determination is repeated as long as the diagnostic condition is not satisfied (NO in step S1).

On the other hand, in a case that the diagnostic condition is determined to be satisfied (YES in step S1), the control situation diagnostic part 117 causes, through the integrated control part 111, the main pump control part 112 to perform measurement of the main pump voltage Vp0 at the time point (step S2), and acquires a value thereof. Alternatively, in a case where the main pump voltage Vp0 is measured continuously under control performed by the main pump control part 112 regardless of whether the diagnostic condition is satisfied, the main pump voltage Vp0 at a time point when the diagnostic condition has just been satisfied may be acquired.

After the main pump voltage Vp0 is acquired, the control situation diagnostic part 117 compares the acquired value and the diagnostic threshold described in the diagnostic threshold data D2 (step S3), and provides a result of comparison to the integrated control part 111.

The diagnostic threshold is herein a lower limit of a range of the value of the main pump voltage Vp0 in which decomposition of NOx can steadily be caused. In other words, decomposition of NOx is not caused as long as the value of the main pump voltage Vp0 is less than the diagnostic threshold. Considering that the oxygen-ion conductive solid electrolyte forming the main pump cell 21 is zirconia and the main pump current Ip0 flows as a limiting current in accordance with the main pump voltage Vp0, it is appropriate to set the diagnostic threshold in a range of 750 mV to 950 mV in a case where the element driving temperature is 700° C. to 900° C. This corresponds to setting the main pump voltage Vp0 when the oxygen concentration is 18% to 900 mV or less. Alternatively, the diagnostic threshold may be changed in accordance with the element driving temperature.

A sensor element having a different structure from the sensor element 101 illustrated in FIG. 1 is the same as the sensor element 101 in that, to prevent decomposition of NOx in a pump cell to pump out oxygen in the measurement gas in the sensor element, it is necessary to set a value of a pump voltage in the pump cell to a value less than the above-mentioned diagnostic threshold.

In a case where the main pump voltage Vp0 is less than the diagnostic threshold (NO in step S3), diagnosis ends as it is (step S4). This means that the controller 110 normally controls operation of the sensor element 101, and decomposition of NOx is not caused in the main pump cell 21.

On the other hand, in a case where the main pump voltage Vp0 is equal to the diagnostic threshold or more (YES in step S3), decomposition of NOx might be caused in the main pump cell 21. To resolve the situation, at least one of a heater temperature (the element driving temperature), a control voltage (target value of the electromotive force V1 in the auxiliary sensor cell 81), and a control current (the auxiliary pump current Ip1 flowing through the auxiliary pump cell 50) is adjusted on a control instruction from the integrated control part 111 (step S5).

In a case where the element driving temperature is a target of adjustment, the integrated control part 111 provides the heater control part 115 with a control instruction to increase the element driving temperature by a predetermined temperature amount. In response to this instruction, the heater control part 115 performs temperature adjustment processing of increasing the heater voltage to be applied to the heater power supply 76 in accordance with the temperature amount.

When the element driving temperature is increased, resistance of zirconia as the solid electrolyte forming the main pump cell 21 decreases, so that the main pump voltage Vp0 decreases with increasing main pump current Ip0. The temperature amount by which the temperature is increased may be determined in accordance with a value of a difference between the main pump voltage Vp0 and the diagnostic threshold, or may be a constant value set in advance. The element driving temperature, however, usually has an upper limit of 900° C.

In a case where the target value of the electromotive force V1 in the auxiliary sensor cell 81 is the target of adjustment, the integrated control part 111 provides the auxiliary pump control part 113 with a control instruction to cause the target value of the electromotive force V1 to be greater than before. In response to this instruction, the auxiliary pump control part 113 controls operation of the auxiliary pump cell 50 so that the new target value is achieved. The above-mentioned processing is referred to as electromotive force adjustment processing. This means that control is performed so as to cause the auxiliary pump voltage Vp1 to be higher than before, thereby to increase the auxiliary pump current Ip1.

The increase in target value of the electromotive force V1 in the auxiliary sensor cell 81 means a decrease in oxygen partial pressure set in the second internal space 40. This has an effect of promoting a flow of oxygen from the first internal space 20 to the second internal space 40, and causing pumping out of oxygen by the auxiliary pump cell 50 in the second internal space 40 to cover pumping out of oxygen by the main pump cell 21 in the first internal space 20 to suppress the increase in main pump voltage Vp0.

In a case where the auxiliary pump current Ip1 flowing through the auxiliary sensor cell 81 is the target of adjustment, the integrated control part 111 provides the auxiliary pump control part 113 with a control instruction to cause the auxiliary pump current Ip1 to be higher than before. In response to this instruction, the auxiliary pump control part 113 controls operation of the auxiliary pump cell 50 so that the auxiliary pump current Ip1 is increased. The above-mentioned processing is referred to as auxiliary pump current adjustment processing. This means that control is performed so as to cause the auxiliary pump voltage Vp1 to be higher than before.

This also has the effect of promoting the flow of oxygen from the first internal space 20 to the second internal space 40, and causing pumping out of oxygen by the auxiliary pump cell 50 in the second internal space 40 to cover pumping out of oxygen by the main pump cell 21 in the first internal space 20 to suppress the increase in main pump voltage Vp0.

FIG. 7 shows an example of a relationship between the auxiliary pump current Ip1 and the main pump voltage Vp0. Specifically, a change of the main pump voltage Vp0 when the value of the auxiliary pump current Ip1 is variously changed while using a model gas having a constant oxygen concentration of 20.5% (the balance being nitrogen) as the measurement gas is shown.

It is confirmed from FIG. 7 that the main pump voltage Vp0 decreases with increasing auxiliary pump current Ip1.

Processing in step S5 is not necessarily required to be performed through selection. For example, one performance suitable in terms of ease and reliability of adjustment is to preferentially adjust the heater temperature (element driving temperature), and, in a case where the main pump voltage Vp0 cannot sufficiently be suppressed only through the adjustment, to perform one or both of the other two adjustment methods.

When the main pump voltage Vp0 is suppressed by any of the methods, diagnosis ends (step S6).

After the control situation diagnostic processing once ends, the control situation diagnostic processing may be performed again at an appropriate timing.

As described above, according to the present embodiment, operation control to the sensor element by the controller in the gas sensor performed in the inappropriate situation in which decomposition of NOx is caused in the main pump cell is suitably suppressed. In particular, even in a gas sensor in which, due to deterioration over time, the main pump voltage increases in a case where the measurement gas has a high oxygen concentration, and thus decomposition of NOx might be caused in the main pump cell, NOx can be measured with accuracy while suppressing the decomposition.

Second Embodiment

In the above-mentioned first embodiment, at least one of the heater temperature (element driving temperature), the control voltage (electromotive force Vp1), and the control current (auxiliary pump current Ip1) is increased in a case where the control situation diagnostic part 117 determines that the main pump voltage Vp0 is equal to the diagnostic threshold or more in the control situation diagnostic processing. From among them, the heater temperature and the control current are known to have a correlation with the magnitude of the offset current.

FIG. 8 shows an example of a relationship between the heater temperature ("DRIVING TEMPERATURE" in FIG. 8) and an actual value of the offset current ("Ip2 offset" in FIG. 8). FIG. 9 shows an example of a relationship between the control current ("Ip1" in FIG. 9) and the actual value of the offset current ("Ip2 offset" in FIG. 9). The term "actual value" of the offset current is herein used to be distinguished from the offset current value fixedly identified under a certain driving condition when the sensitivity characteristics are identified. A value $R^2$ shown in each of FIGS. 8 and 9 is the determination coefficient (the square of the correlation coefficient R) of an approximate curve.

As shown in FIGS. 8 and 9, the actual value of the offset current tends to increase with increasing heater temperature and with increasing control current. This means that, in a case where the heater temperature or the control current is increased by performing the control situation diagnostic processing shown in the first embodiment, the actual value of the offset current, which is originally required to be a fixed value, increases.

It is thus considered that, in a case where the heater temperature or the control current is increased in the control situation diagnostic processing, an actual offset current value becomes greater in the gas sensor 100 after the processing, than a value (a kind of an initial value of the offset current value) stored in the controller 110 as a result of identification of the sensitivity characteristics. This suggests a possibility that accuracy of the NOx current Ip2 measured after the control situation diagnostic processing is reduced compared with that before the control situation diagnostic processing.

As can be seen from FIGS. 8 and 9, the offset current value increases significantly when the heater temperature or the control current is increased greatly in the control situation diagnostic processing. In such a case, particularly in a case where NOx having a low concentration to generate a smaller NOx current Ip2 is a target of measurement, the risk of reduction in accuracy increases through the measurement.

In the present embodiment, while suppressing decomposition of NOx in the main pump cell by performing the control situation diagnostic processing in a similar manner to that in the first embodiment, reduction in measurement accuracy caused by the increase in offset current value caused as a result of the control situation diagnostic processing is suitably suppressed in post-processes.

Figure 10:
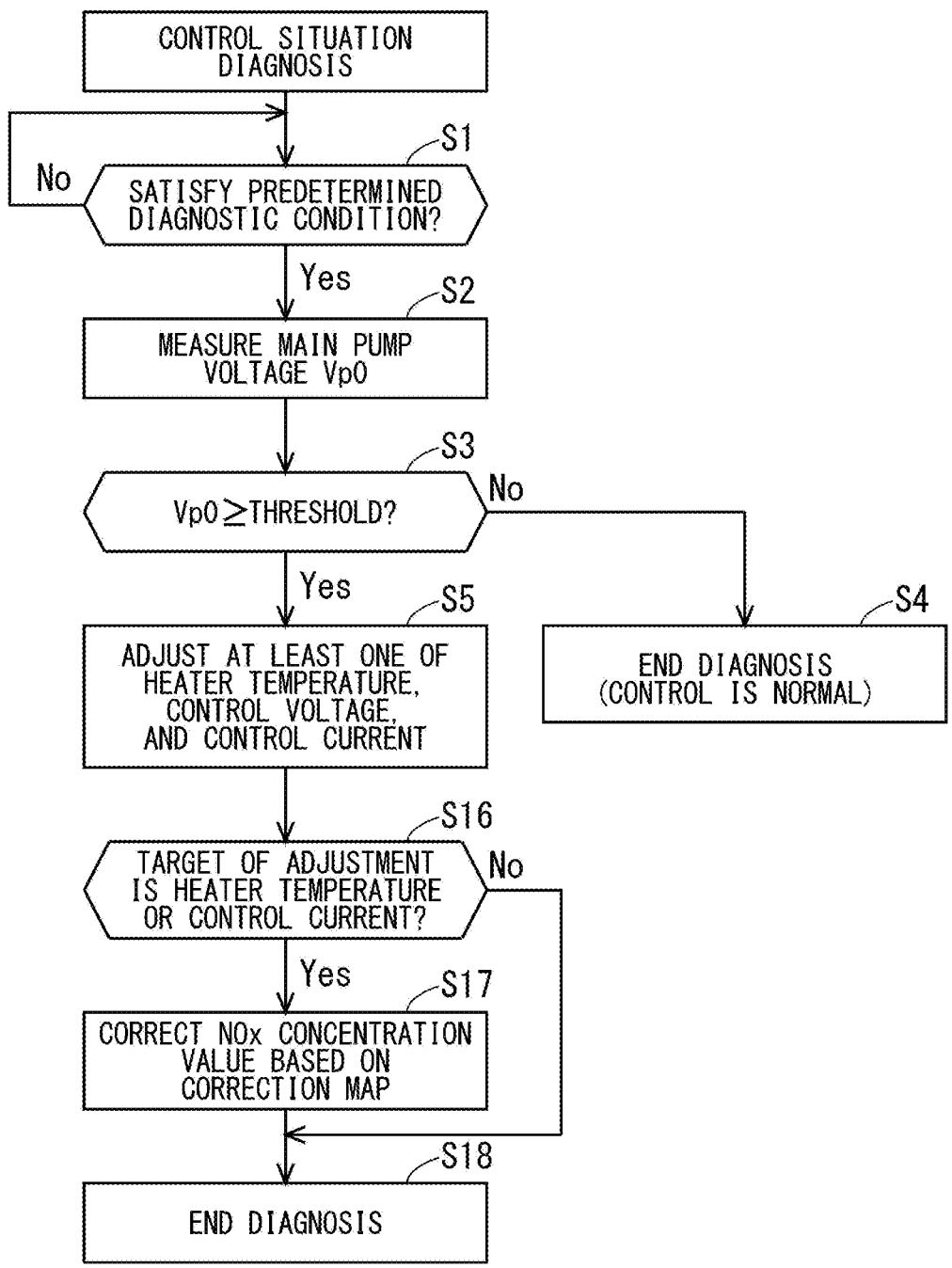
FIG. 10 shows a flow of the control situation diagnostic processing in the gas sensor 100 along with post-processes.

FIG. 10 shows a flow of the control situation diagnostic processing in the gas sensor 100 performed in the present embodiment along with the post-processes. Specifically, processing in step S1 to step S5 is the same as the control situation diagnostic processing in the first embodiment, and thus detailed description thereof is omitted.

In the present embodiment, after step S5 of the control situation diagnostic processing ends, the concentration calculating part 116 then corrects, based on a correction map stored in the controller 110 in advance, a NOx concentration value obtained from the NOx current Ip2 and the sensitivity characteristics (step S17), in a case where the target of adjustment in step S5 is the element driving temperature (heater temperature) or the auxiliary pump current Ip1 (control current) flowing through the auxiliary sensor cell 81 (YES in step S16).

The correction map is a two-dimensional data set showing the relationship between the heater temperature or the control current and the offset current as in the graphs shown in FIGS. 8 and 9, for example. Alternatively, the correction map may be a three-dimensional data set showing a comprehensive relationship among the heater temperature, the control current, and the offset current. Details of a description form thereof are not particularly limited as long as the concentration calculating part 116 can suitably perform correction.

The correction map is generated in advance prior to actual use of the gas sensor 100 by measuring the NOx current Ip2 at various heater temperatures and control currents using model gases not containing NOx, and is held by the controller 110 (more particularly, by memory thereof).

For example, in a case where the graph shown in FIG. 8 is applied as the correction map in a gas sensor 100 in which the offset current value is identified as 0.04 μA under a condition that the element driving temperature is 800° C., if the element driving temperature is increased to 850° C. in step S5 as a result of determination in step S3, the offset current value is changed to 0.08 μA based on the correction map. The NOx concentration value obtained based on the sensitivity characteristics is corrected using the new offset current value. Reduction in NOx measurement accuracy caused by the increase in offset current value is thereby suitably suppressed.

There can be various specific ways to perform correction. For example, the NOx concentration value may be obtained based on the sensitivity characteristics after subtracting the increase in offset current value from the value of the NOx current Ip2, or, after correcting the sensitivity characteristics themselves using the new offset current value, the NOx concentration value may be obtained based on the sensitivity characteristics after correction.

When the NOx concentration value is corrected, a series of processes ends (step S18).

Also in a case where the target of adjustment in step S5 is the electromotive force V1 (control voltage) (NO in step S16), processing ends as it is (step S18).

As described above, in the present embodiment, the control situation diagnostic processing is performed in a similar manner to that in the first embodiment, and thus, it is suitably suppressed that operation control to the sensor element by the controller in the gas sensor is performed in the inappropriate situation in which decomposition of NOx is caused in the main pump cell.

In addition, even in a case where the offset current increases with the control situation diagnostic processing, reduction in NOx measurement accuracy caused by the increase is suitably suppressed.

<Modification>

In the above-mentioned embodiment, the measurement electrode 44 is placed in the second internal space 40 to be covered with the fourth diffusion control part 45 functioning as the porous protective film and providing the predetermined diffusion resistance to the measurement gas, and the amount of NOx flowing into the measurement electrode 44 is limited by the fourth diffusion control part 45. Alternatively, however, a third internal space communicating with the second internal space 40, for example, through a slit-like or porous diffusion control part providing, to the measurement gas, diffusion resistance equivalent to the diffusion resistance provided by the fourth diffusion control part 45 may be provided, and the measurement electrode 44 may be provided in the third internal space.

Examples

A gas sensor 100 (hereinafter, a new sensor) including a new sensor element 101 and a gas sensor 100 (hereinafter, a deteriorated sensor) obtained by placing a new sensor element 101 manufactured under the same condition in air, and conducting the continuous operation test for 3000 hours at 800° C. to reproduce a deteriorated state were prepared, and, for each of the gas sensors 100, model gas measurement targeted at four model gases having different oxygen concentrations of 0%, 5%, 10%, and 18% while having a constant NO concentration of 500 ppm (the balance being $N_2$ in each of the model gases) was performed. In each case, the element driving temperature was 800° C., the target value of the electromotive force V1 in the auxiliary sensor cell 81 was 350 mV, and a target value of the auxiliary pump current Ip1 was 7 μA.

As for the deteriorated sensor, model gas measurement (hereinafter, Example 1) in which the driving temperature was changed to 850° C., model gas measurement (hereinafter, Example 2) in which the target value of the electromotive force V1 in the auxiliary sensor cell 81 was changed to 400 mV, and model gas measurement (hereinafter, Example 3) in which the auxiliary pump current Ip1 flowing through the auxiliary sensor cell 81 was changed to 14 μA were performed to correspond to the respective three adjustment methods in the step S5 of the control situation diagnostic processing performed in the above-mentioned embodiment. Each of the cases was based on the assumption that the diagnostic threshold was set to 950 mV.

Figure 11A:
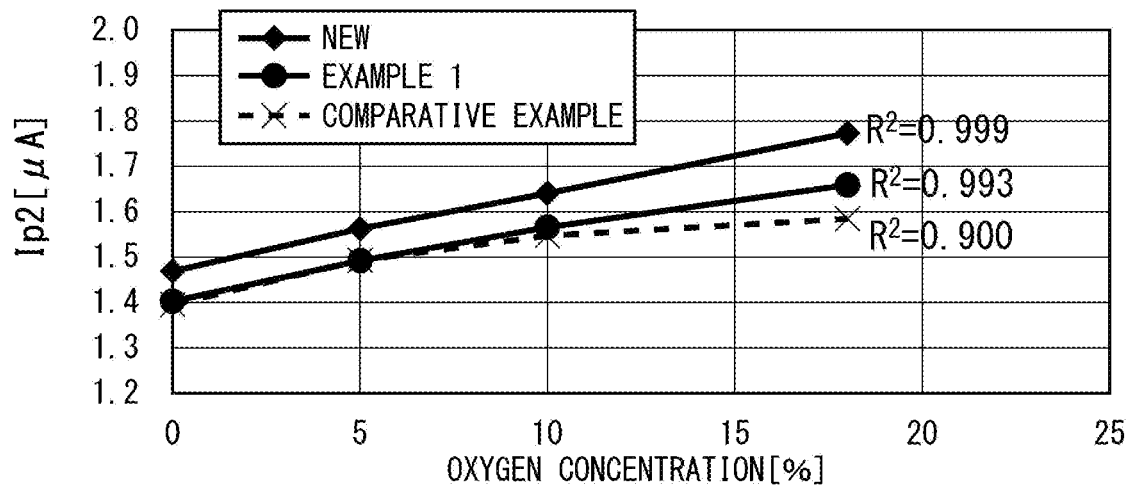
FIGS. 11A to 11C are plots of NOx currents Ip2 obtained through model gas measurement using a new sensor, a deteriorated sensor, and Examples 1 to 3 against the oxygen concentrations of the model gases.
Figure 11B:
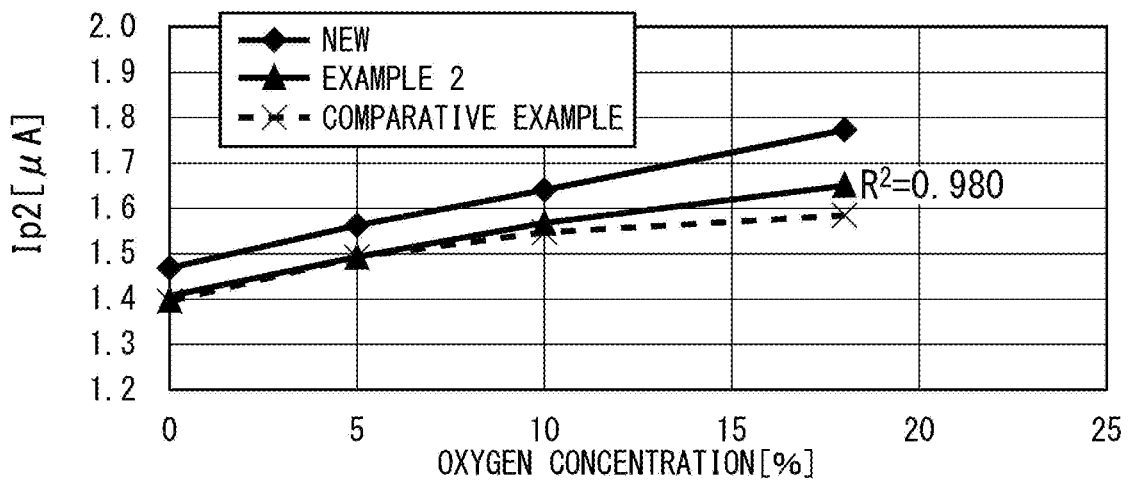
Figure 11C:
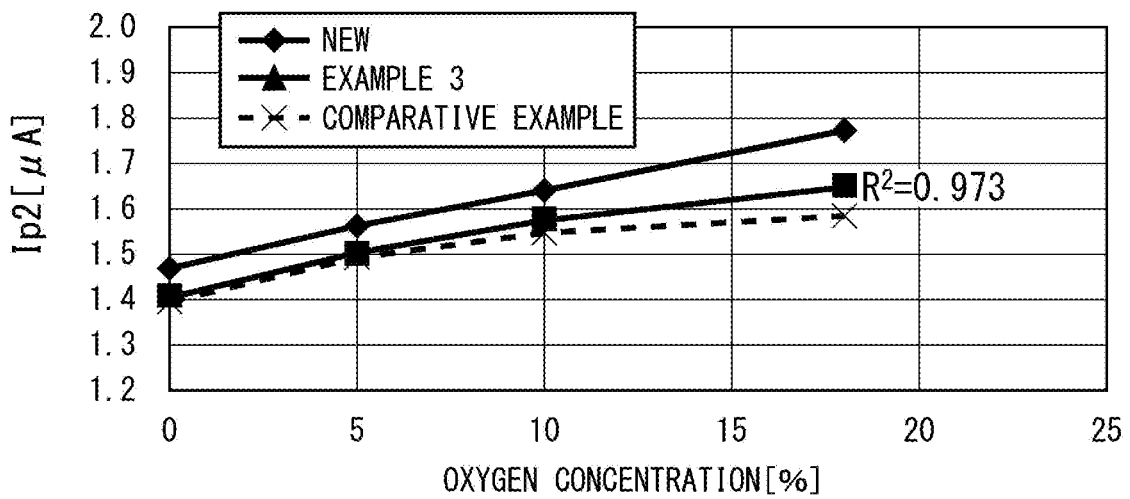

FIGS. 11A to 11C are plots of NOx currents Ip2 obtained through the model gas measurement against the oxygen concentrations of the model gases. FIGS. 11A, 11B, and 11C respectively show results in Example 1, Example 2, and Example 3 along with a result for the new sensor and a result for the deteriorated sensor before adjustment processing. In each of FIGS. 11A to 11C, the result for the new sensor is shown as "NEW", and the result for the deteriorated sensor is shown as "COMPARATIVE EXAMPLE".

As representatively shown in FIG. 11A, for the new sensor, there was a linear change of a monotonous increase between the NOx current Ip2 and the oxygen concentration, and the determination coefficient $R^2$ determined by a result of a plot had a high numerical value of 0.999, while, in a case of the deteriorated sensor, the value of the NOx current Ip2 was generally smaller than that for the new sensor, and leveled off when the oxygen concentration was between 10% and 18% while having a tendency to monotonously increase when the oxygen concentration was 10% or less. The main pump voltage Vp0 had a maximum value of 900 mV, while the determination coefficient $R^2$ was limited to 0.900.

As shown in FIGS. 11A to 11C, however, in Examples 1 to 3 in which three types of adjustment processing were performed for the deteriorated sensor, the value of the NOx current Ip2 was smaller than that for the new sensor, but the tendency to monotonously increase seen in the deteriorated sensor only when the oxygen concentration was 10% or less was maintained when the oxygen concentration was between 10% and 18%. The determination coefficients in Examples 1, 2, and 3 were respectively 0.993, 0.980, and 0.973, which were almost equivalent to the determination coefficient for the new sensor. The values of the main pump voltage Vp0 when the oxygen concentration was 18% in Examples 1, 2, and 3 were respectively 700 mV, 765 mV, and 780 mV, which were smaller than 900 mV.

The results suggest that the three types of adjustment processing performed in step S5 can improve control of the gas sensor and further can secure NOx concentration measurement accuracy in the gas sensor deteriorated over time.

The influence of general reduction of the value of the NOx current Ip2 on measurement can be canceled by applying the sensitivity characteristics in accordance with reduction of the value of the current.

While the invention has been shown and described in detail, the foregoing description is in all aspects illustrative and not restrictive. It is therefore understood that numerous modifications and variations can be devised without departing from the scope of the invention.

What is claimed is:

1. A limiting-current type gas sensor measuring concentration of NOx in a measurement gas, said gas sensor comprising:
   a sensor element having a base part made of an oxygen-ion conductive solid electrolyte, said sensor element including:
      a gas inlet through which said measurement gas is introduced from an external space;
      a first internal space communicating with said gas inlet under predetermined diffusion resistance;
      a main pump cell as an electrochemical pump cell including an inner pump electrode located to face said first internal space, an out-of-space pump electrode located to face a space other than said first internal space, and said solid electrolyte located between said inner pump electrode and said out-of-space pump electrode;

a measurement electrode located inside said sensor element, at least one diffusion control part being located between said measurement electrode and said first internal space;

a measurement pump cell as an electrochemical pump cell including said measurement electrode, said out-of-space pump electrode, and said solid electrolyte located between said measurement electrode and said out-of-space pump electrode;

a reference electrode located inside said sensor element and capable of being in contact with a reference gas; and a heater part buried in said sensor element and heating said sensor element; and a controller controlling operation of said gas sensor, said controller including a processor and a memory and being configured to:

perform condition determination processing of determining whether said gas sensor satisfies a predetermined diagnostic condition when said gas sensor is in an operation state capable of measuring a NOx concentration;

perform diagnostic processing of diagnosing a situation of control to said gas sensor in a case that said gas sensor is determined to satisfy said diagnostic condition; and perform adjustment processing of adjusting a condition under which said gas sensor is controlled in accordance with a result of diagnosis in said diagnostic processing, wherein said gas sensor is put into said operation state capable of measuring said NOx concentration at least when:

said heater part heats said sensor element to a predetermined element driving temperature;

a main pump voltage is applied to said main pump cell so that an oxygen concentration in said first internal space is constant; and a measurement pump voltage is applied to said measurement pump cell so that oxygen generated through decomposition of NOx in said measurement electrode is pumped out, in said diagnostic processing, said main pump voltage is compared with a diagnostic threshold set in advance as a value of a voltage not causing decomposition of NOx in said main pump cell, a temperature adjustment element performs temperature adjustment processing as said adjustment processing, said temperature adjustment processing is processing to cause, in a case that said main pump voltage is diagnosed to be equal to said diagnostic threshold or more in said diagnostic processing, said main pump voltage to be less than said diagnostic threshold, at least in a way that said heater part increases said element driving temperature in said operation state by a predetermined increase amount, said controller is further configured to:

perform electromotive force adjustment processing as said adjustment processing; and perform auxiliary pump current adjustment processing as said adjustment processing, said electromotive force adjustment processing is processing to promote pumping out of oxygen with an auxiliary pump cell and thereby to cause said main pump voltage to be less than said diagnostic threshold, in a way of increasing a target value of electromotive force generated between an auxiliary pump electrode and said reference electrode set in accordance with a target oxygen concentration in a second internal space, said auxiliary pump current adjustment processing is processing to promote pumping out of oxygen with said auxiliary pump cell and thereby to cause said main pump voltage to be less than said diagnostic threshold, in a way of increasing a target value of an auxiliary pump current flowing through said auxiliary pump cell, and said adjustment processing includes at least one of said electromotive force adjustment processing and said auxiliary pump current adjustment processing in addition to said temperature adjustment processing.

2. The gas sensor according to claim 1, wherein said sensor element further includes:

said second internal space communicating with said first internal space under predetermined diffusion resistance; and said auxiliary pump cell as an electrochemical pump cell including said auxiliary pump electrode located to face said second internal space, said out-of-space pump electrode, and said solid electrolyte located between said auxiliary pump electrode and said out-of-space pump electrode, a diffusion control part is at least located between said measurement electrode and said second internal space, said gas sensor further includes:

a first variable power supply to apply said main pump voltage between said out-of-space pump electrode and said inner pump electrode;

a second variable power supply to apply an auxiliary pump voltage between said out-of-space pump electrode and said auxiliary pump electrode; and a third variable power supply to apply said measurement pump voltage between said out-of-space pump electrode and said measurement electrode, and said gas sensor is put into said operation state capable of measuring said NOx concentration further when:

said first variable power supply applies said main pump voltage so that said oxygen concentration in said first internal space is constant;

said second variable power supply applies said auxiliary pump voltage so that an oxygen concentration in said second internal space is constant; and said third variable power supply applies said measurement pump voltage so that oxygen generated through decomposition of NOx in said measurement electrode is pumped out.

3. The gas sensor according to claim 2, wherein in said electromotive force adjustment processing, a target value of electromotive force generated between said inner pump electrode and said reference electrode, set in accordance with a target oxygen concentration in said first internal space, is decreased.

4. The gas sensor according to claim 3, wherein said controller is further configured to:

obtain a value of said concentration of NOx in said measurement gas based on a magnitude of a current flowing through said measurement pump cell; and correct said value of said obtained concentration of NOx based on at least one of said element driving temperature after the increase in said temperature adjustment processing and said auxiliary pump current after the increase in said auxiliary pump current adjustment processing.

5. The gas sensor according to claim 4, wherein said controller is further configured to:

store a correction map identified in advance and indicating a relationship between an offset current and at least one of said element driving temperature and said auxiliary pump current, said offset current being a current flowing through said measurement pump cell when said measurement gas does not contain NOx; and correct said value of said concentration of NOx based on said correction map.

6. The gas sensor according to claim 2, wherein
said controller is further configured to:
  obtain a value of said concentration of NOx in said measurement gas based on a magnitude of a current flowing through said measurement pump cell; and
  correct said obtained value of said concentration of NOx based on at least one of said element driving temperature after the increase in said temperature adjustment processing and said auxiliary pump current after the increase in said auxiliary pump current adjustment processing.

7. The gas sensor according to claim 6, wherein
said controller is further configured to:
store a correction map identified in advance and indicating a relationship between an offset current and at least one of said element driving temperature and said auxiliary pump current, said offset current being a current flowing through said measurement pump cell when said measurement gas does not contain NOx; and
correct said value of said concentration of NOx based on said correction map.

8. The gas sensor according to claim 7, wherein
said element driving temperature is set in a range of 700° C. to 900° C.,
in said condition determination processing, it is determined that said diagnostic condition is satisfied at least when temperature of said sensor element has reached said element driving temperature and said measurement gas introduced into said sensor element is an air atmosphere, and
said diagnostic threshold is set in a range of 750 mV to 950 mV.

9. The gas sensor according to claim 6, wherein
said element driving temperature is set in a range of 700° C. to 900° C.,
in said condition determination processing, it is determined that said diagnostic condition is satisfied at least when temperature of said sensor element has reached said element driving temperature and said measurement gas introduced into said sensor element is an air atmosphere, and
said diagnostic threshold is set in a range of 750 mV to 950 mV.

10. The gas sensor according to claim 1, wherein
said element driving temperature is set in a range of 700° C. to 900° C.,
in said condition determination processing, it is determined that said diagnostic condition is satisfied at least when temperature of said sensor element has reached said element driving temperature and said measurement gas introduced into said sensor element is an air atmosphere, and
said diagnostic threshold is set in a range of 750 mV to 950 mV.

* * * * *